US007731905B2

(12) United States Patent
Tsuruoka

(10) Patent No.: US 7,731,905 B2
(45) Date of Patent: Jun. 8, 2010

(54) PROCESS FOR PRODUCING PROBE CARRIER AND APPARATUS THEREOF

(75) Inventor: Yuji Tsuruoka, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 1351 days.

(21) Appl. No.: 10/102,706

(22) Filed: Mar. 22, 2002

(65) Prior Publication Data

US 2002/0135632 A1    Sep. 26, 2002

(30) Foreign Application Priority Data

Mar. 26, 2001   (JP)   .............................. 2001-087954
Mar. 26, 2001   (JP)   .............................. 2001-087955

(51) Int. Cl.
*B01L 3/02* (2006.01)
(52) U.S. Cl. .......................... 422/100; 422/99; 422/11; 347/19; 347/40; 347/43; 347/78; 700/241; 436/180
(58) Field of Classification Search ........... 422/99–101; 347/19, 40, 43, 78; 436/180; 700/241
See application file for complete search history.

(56) References Cited

U.S. PATENT DOCUMENTS

| | | | |
|---|---|---|---|
| 4,313,124 A | 1/1982 | Hara | |
| 4,345,262 A | 8/1982 | Shirato et al. | |
| 4,459,600 A | 7/1984 | Sato et al. | |
| 4,463,359 A | 7/1984 | Ayata et al. | |
| 4,558,333 A | 12/1985 | Sugitani et al. | |
| 4,723,129 A | 2/1988 | Endo et al. | |
| 4,740,796 A | 4/1988 | Endo et al. | |
| 5,338,688 A * | 8/1994 | Deeg et al. | ............ 436/180 |
| 5,508,200 A | 4/1996 | Tiffany et al. | |
| 5,677,197 A | 10/1997 | Gordon et al. | |
| 6,001,309 A * | 12/1999 | Gamble et al. | ............ 422/100 |
| 6,168,261 B1 | 1/2001 | Miyake et al. | |
| 6,890,760 B1 * | 5/2005 | Webb | ............ 436/180 |

FOREIGN PATENT DOCUMENTS

| | | |
|---|---|---|
| EP | 0 816 089 | 1/1998 |
| EP | 0 895 082 | 2/1999 |
| EP | 1 025 902 | 8/2000 |
| EP | 1 048 723 | 11/2000 |
| EP | 1 231 062 | 8/2002 |

(Continued)

*Primary Examiner*—Jyoti Nagpaul
(74) *Attorney, Agent, or Firm*—Fitzpatrick, Cella, Harper & Scinto

(57) ABSTRACT

An apparatus produces a probe carrier by discharging plural kinds of liquids respectively containing plural kinds of probes capable of specifically bonding to a target substance on a carrier. The apparatus includes a liquid discharge device, a positioning device for determining a position between the liquid discharge device and the carrier, and moving the carrier in the scanning direction, an application information detector to detect application information of discharged liquids, and a defective spot detector to detect defective spots where the liquids are not applied. Also included are a discharge data forming device for forming data on the defective spots, a processor for counting a number of redrawings, and a secondary scanning direction driver for relatively moving the carrier in a secondary scanning direction. In the apparatus, redrawing is performed according to discharge data, and when the number of redrawings exceeds a prescribed number, a message of abnormality is outputted.

21 Claims, 12 Drawing Sheets

FOREIGN PATENT DOCUMENTS

| | | |
|---|---|---|
| EP | 1 232 870 | 8/2002 |
| GB | 2355716 | 5/2001 |
| JP | 59-123670 | 7/1984 |
| JP | 59-138461 | 8/1984 |
| JP | 6-79956 | 3/1994 |
| JP | 11-988 | 1/1999 |
| JP | 11-187900 | 7/1999 |
| JP | 2001-021558 | 1/2001 |

* cited by examiner

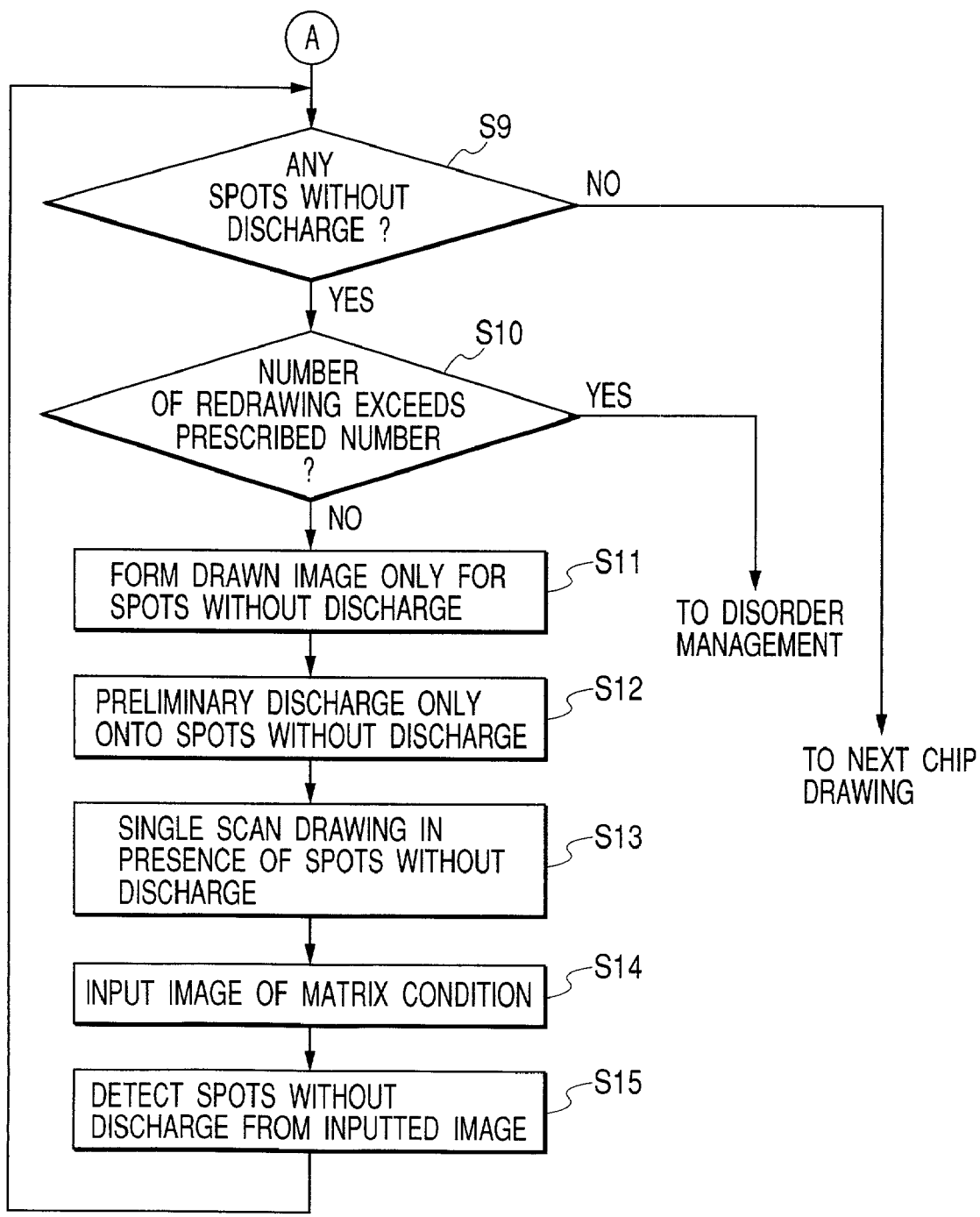

| FIG. 2A |
| FIG. 2B |

PROCESS FOR PRODUCING PROBE CARRIER AND APPARATUS THEREOF

BACKGROUND OF THE INVENTION

1. Field of the Invention

The present invention relates to an apparatus for producing a probe carrier by discharging a liquid from a liquid discharging device on a carrier according to discharge data inputted from a host computer or the like, and particularly to a production apparatus of a probe carrier, which is suitable for use in preparation of a DNA microchip or the like by discharging a plurality of probe solutions from a plurality of nozzles provided in a liquid discharging device on a carrier such as a glass substrate and a production process using such an apparatus.

2. Related Background Art

When analysis of a base sequence of a gene DNA, a genetic diagnosis or the like is performed, it is necessary to select a DNA having the intended base sequence using plural kinds of probes. As a means for providing the plural kinds of probes used in this selecting work, there is a DNA microchip called a microarray, probe array, DNA chip or the like. In the DNA microchip, plural kinds of probes are arranged in a state of a two-dimensional array on a solid-phase substrate. About several tens to several thousands of different probes are generally arranged. With respect to a process for preparing this DNA microchip by means of a liquid discharging device, there has been proposed a process in which liquids respectively containing probes are injected and attached on a solid-phase substrate by a liquid discharging device to form spots respectively containing the probes on the solid-phase substrate as disclosed in Japanese Patent Application Laid-Open No. 11-187900.

Since probe solutions are expensive, probe solutions spotted at respective spots on a DNA microchip are generally all different, and the spots are required to be arranged at a high density, the amount of the probe solutions spotted is also controlled to a necessary minimum. For the same reasons, operations consuming a discharged liquid, such as a sucking operation of the discharged liquid and a preliminarily discharging operation, which are generally conducted in ordinary drawing apparatus or recording apparatus, must be avoided as much as possible. However, the sucking operation of the discharged liquid in an ink-jet head using a printing ink is intended to refill the discharged liquid into a nozzle and refresh the discharged liquid in the nozzle. On the other hand, the preliminary discharge is intended to make a discharge condition better. Therefore, when the frequency of these operations is lessened, the discharge condition becomes unstable, resulting in occurrence of problems such as discharge failure.

In the conventional drawing apparatus utilizing a liquid discharging device, methods for avoiding a failure of an image drawn due to discharge failure of the liquid discharging device include methods disclosed in Japanese Patent Application Laid-Open Nos. 06-079956 and 11-000988. The method disclosed in Japanese Patent Application Laid-Open No. 06-079956 is such that an image pattern for specifying non-discharging nozzles is drawn prior to an operation of drawing a desired image, a processing of detecting non-discharging nozzles is performed according to this pattern, and image dots drawn by the non-discharging nozzles are drawn by other substitutive nozzles if the non-discharging nozzles are detected, thereby obtaining the desired image. The method disclosed in Japanese Patent Application Laid-Open No. 11-000988 is such that a processing of detecting non-discharging nozzles is performed in the same manner as described above, and image dots originally drawn by the non-discharging nozzles are supplemented by prolix nozzles not used in an ordinary drawing operation if the non-discharging nozzles are detected.

However, the present inventors have found that when it is attempted to use such a drawing apparatus for printing an image on a recording medium such as paper as described above in preparation of a DNA microchip, expensive probe solutions are wasted more than the preparation needs by the following three reasons, thereby incurring rise in the preparation cost of the DNA microchip.

(1) A discharge failure-detecting pattern for specifying non-discharging nozzles must be drawn.

(2) When a new non-discharging nozzle occurs during drawing of a desired image, the image drawing itself comes to nothing.

(3) Since a high yield cannot be maintained unless discharge is always stabilized, preliminary discharge must be frequently conducted.

SUMMARY OF THE INVENTION

It is therefore an object of the present invention to reduce a preparation cost by controlling waste of probe solutions to a minimum and improving a preparation yield of an immobilized probe chip such as a DNA microchip The above object can be achieved by the present invention described below.

According to the present invention, there is thus provided a production apparatus for producing a probe carrier by discharging plural kinds of liquids respectively containing plural kinds of probes capable of being specifically bonded to a target substance on a carrier, comprising:

a liquid discharging device having nozzles for discharging the liquids respectively containing the plural kinds of probes capable of being specifically bonded to the target substance on the carrier;

a positioning means for determining a relative position between the liquid discharging device and the carrier;

an application information detector for detecting an application information of a liquid discharged on the carrier from the liquid discharging device on the basis of discharge data;

a defective spot detector for detecting that the liquids are not applied to spots where the respective liquids should be applied by comparing the discharge data with the application information detected by the application information detector; and a discharge data forming means for forming discharge data as to the defective spots on the basis of the defective spot information from the defective spot detector, wherein the liquids are respectively applied to the defective spots from the liquid discharging device according to the discharge data formed by the discharge data forming means.

According to the present invention, there is also provided a process for producing a probe carrier by discharging plural kinds of liquids respectively containing plural kinds of probes capable of being specifically bonded to a target substance on a carrier, comprising the steps of:

respectively discharging the plural kinds of liquids from a liquid discharging device on the basis of discharge data while changing a relative position between the liquid discharging device and the carrier, thereby applying the liquids to the carrier;

detecting application information of the liquids applied to the carrier;

detecting defective spots where the liquids are not applied, to which spots the respective liquids should be applied on the basis of the discharge data, by comparing the discharge data with the application information detected; and discharging the liquids to the detected defective spots from the liquid discharging device when the defective spots are detected, thereby applying the liquids to the defective spots.

In the present invention, the liquid discharging device arranged in opposition to the carrier is moved in a main scanning direction, and desired liquid application information of the liquids applied to the carrier is first formed according to original discharge data inputted upon a drawing operation according to the inputted original discharge data on the basis of position information of the liquid discharging device in the main scanning direction. The liquid application information of the liquids formed on the carrier is then detected to compare the liquid application information detected with the original discharge data, thereby detecting defective spots, i.e., positions where the liquids are not applied, to which positions the respective liquids should be applied in the liquid application information. When the defective spots are detected, discharge data for the defective spots for discharging necessary liquids again from the liquid discharging device to correct the defective spots is formed to apply the necessary liquids again to the defective spots of a pattern first formed on the carrier on the basis of this data. The liquid application information based on the original discharge data first inputted can be completed on the carrier by this reapplication of the liquids. Incidentally, the reapplication of the liquids can be completed with more certainty by conducting preliminary discharge with nozzles that caused the defective spots prior to the application of the liquids to the defective spots. Further, defective spots in the first discharge can be reduced by adding preliminary discharge when injecting the probe solutions or starting up the apparatus.

DETAILED DESCRIPTION OF THE PREFERRED EMBODIMENTS

The embodiments of the present invention will hereinafter be described with reference to the accompanying drawings.

Figure 3:
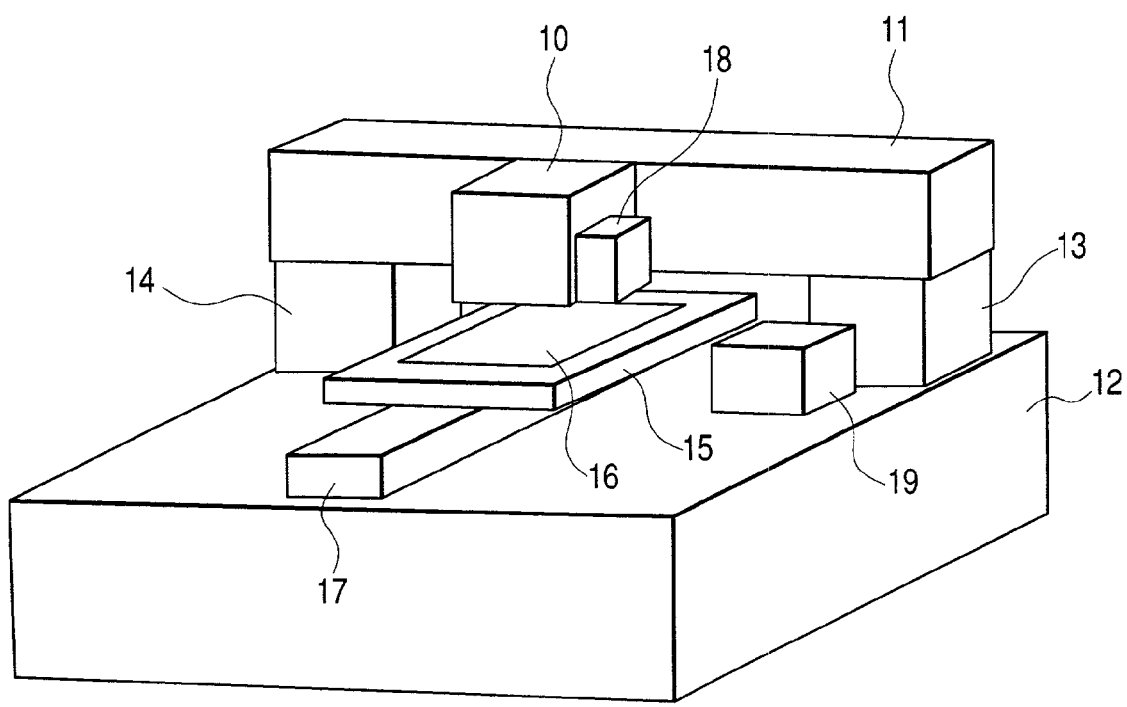
FIG. 3 schematically illustrates an exemplary drawing apparatus according to the present invention.

With reference to FIG. 3, the whole structure of a drawing apparatus according to this embodiment will now be described. FIG. 3 is a typical perspective view of the drawing apparatus. The drawing apparatus is such an apparatus that a drawing head 8 (see FIGS. 9 and 10) composed of a liquid discharging device 1 (see FIGS. 12 to 14), which will be described subsequently, is mounted on a carriage 10, and probe solutions are discharged from the drawing head 8 to apply them to a carrier 16, thereby producing such a probe carrier 7 (see FIG. 8) as described below.

The carriage 10 functions as a holder for holding the drawing head 8 and is fixed to and supported on a slider part of a CR linear motor 11 in such a manner that it can be moved in a main scanning direction. Since the total weight of the carriage 10 and the drawing head 8 mounted thereon may exceed 10 kg in some cases, the CR linear motor 11 supporting them is firmly fixed by two right and left bases 13, 14 fixed to a platen 12. On the other hand, a stage 15 capable of sucking a carrier 16 on an upper surface thereof by vacuum suction is arranged under the carriage 10. The stage 15 is supported movably in a secondary scanning direction substantially perpendicular to the moving direction (main scanning direction) of the carriage 10 on an LF linear motor 17 fixed to the platen 12.

Such a drawing apparatus is so constructed that a relative position between the carrier 16 and the drawing head 8 can be arbitrarily changed by moving the carriage 10, and thus the drawing head 8 held thereon, by the CR linear motor 11 and moving the stage 15, and thus the carrier 16 held thereon, to spot probe solutions at any positions on the carrier 16 by the drawing head 8. More specifically, a positioning means for determining a relative position between the liquid discharging device 1 and the carrier 16 is constructed by the stage 15, CR linear motor 11, LF linear motor 17, platen 12 and bases 13, 14.

A preliminary discharge reservoir 19 for receiving probe solutions preliminarily discharged is provided at a right end in a carriage moving range to provide for the preliminary discharge of the drawing head 8. An image sensor unit (application information detector) 18 for inputting an image on the surface of the carrier is provided on a side surface of the carriage 10 in such a manner that the condition of the probe solutions spotted in the form of a matrix can be observed.

Figure 11:
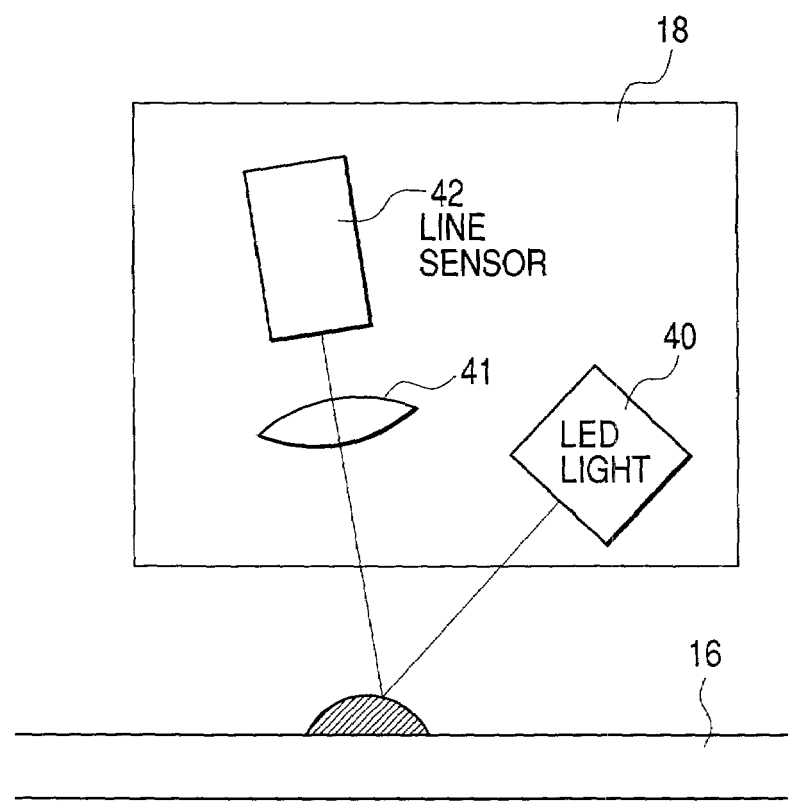
FIG. 11 schematically illustrates an exemplary image sensor unit.

FIG. 11 schematically illustrates the construction of an exemplary image sensor unit 18. This image sensor unit 18 has an LED light 40 using LED for lighting a spot on the carrier 16 and a line sensor 42 for inputting reflected light of light from the LED light 40 on the spot on the carrier 16 through a cylindrical lens 41. The lighting direction of the light from the LED light and the incident direction of the reflected light on the line sensor 42 are adjusted in such a manner that the light reflected on the surface of the carrier 16 when no probe solution is applied in spots does not reach the line sensor 42, while the reflected light when the probe solutions are applied is incident on the line sensor 42. This image sensor unit 18 does not have such a large-scaled optical system that the conditions of the probe solutions applied in spots can be grasped, but has a sufficient construction to distinguish between presence and absence of the probe solutions at respective spots the existing positions of which have been known in advance.

Figure 5:
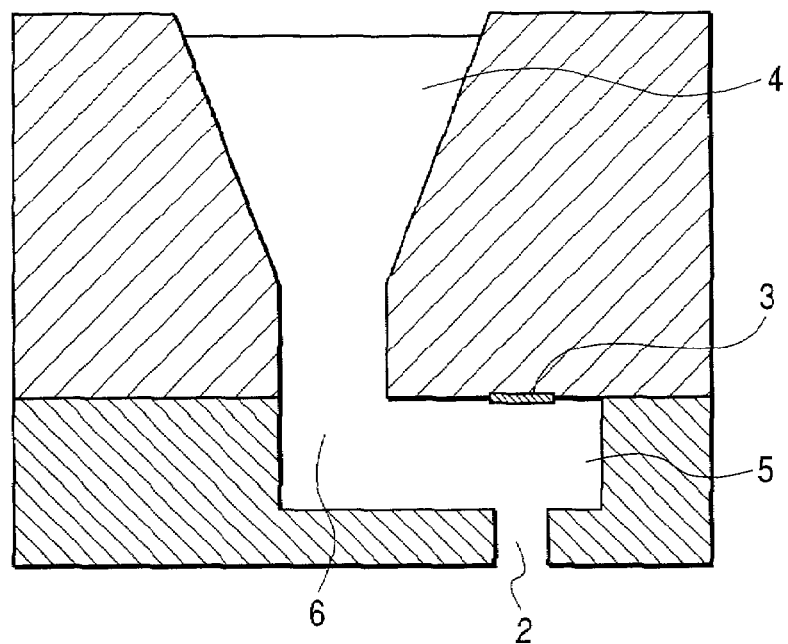
FIG. 5 is an enlarged longitudinal cross-sectional view of an exemplary liquid discharging part including an orifice in a liquid discharging direction (cross-sectional view taken along line 5-5 in FIG. 13).
Figure 12:
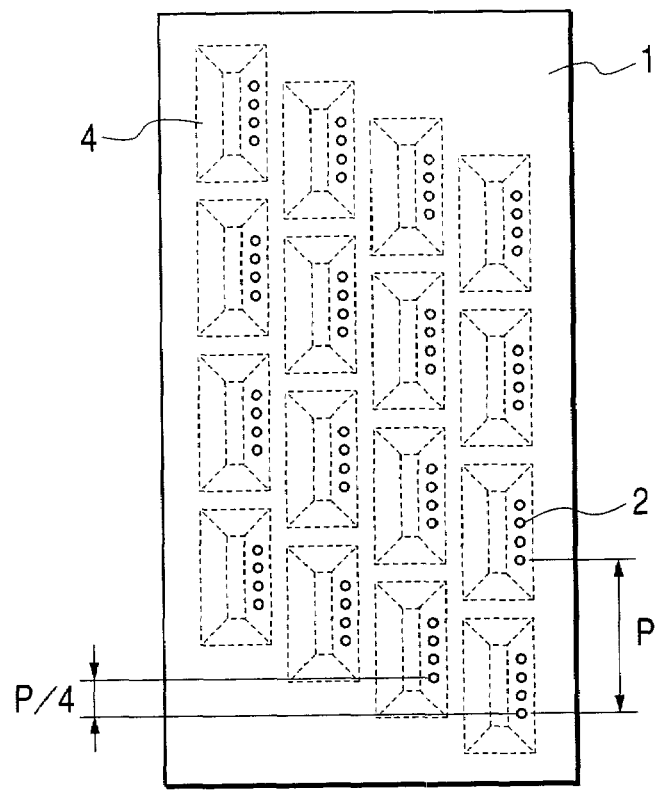
FIG. 12 is a plan view of a liquid discharging device making up a drawing head mounted on a carriage of the drawing apparatus shown in FIG. 3.
Figure 13:
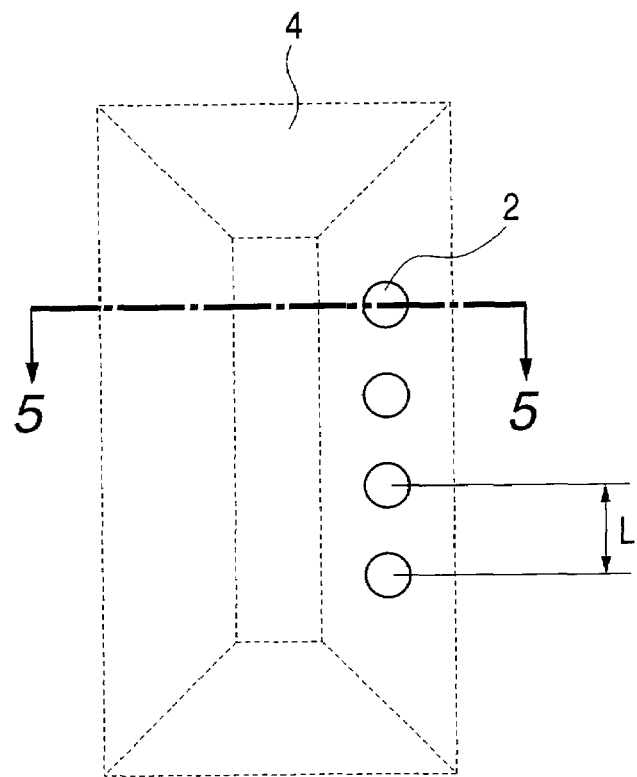
FIG. 13 is an enlarged plan view of a part related to a probe solution in the liquid discharging device shown in FIG. 12.

With reference to FIGS. 12 and 13, the construction of the liquid discharging device 1 making up the drawing head 8 mounted on the carriage 10 will be described. FIG. 12 is a plan view of the liquid discharging device 1 viewed from a side in which orifices 2 discharging liquids have been opened. FIGS. 13 and 5 are enlarged views of a liquid discharging part related to the discharge of a probe solution in this liquid discharging device 1. FIG. 13 is a plan view viewed from a side in which the orifices 2 have been opened, and FIG. 5 is a cross-sectional view taken along line 5-5 in FIG. 13.

The drawing apparatus for production of a probe carrier is required to discharge many kinds of probe solutions arranged on a probe carrier. Thus, the drawing apparatus must be equipped with solution reservoirs (liquid container parts) by the number of kinds of probes arranged on the probe carrier and nozzles for respectively discharging the probe solutions in communication with the reservoirs. The liquid discharging device 1 according to this embodiment has 16 (4×4) solution reservoirs 4 in total, which can respectively contain probe solutions of different kinds from one another. The solution reservoirs 4 are arranged at intervals P of about ⅕ inches (5.08 mm) both in length and width. The solution reservoirs 4 have such an arrangement that rows of each four reservoirs in length are lined by four rows in width. The solution reservoirs 4 of each row are arranged with a difference by an interval of P/4 in a lengthwise direction from the solution reservoirs 4 of the adjacent row.

In this embodiment, in order to produce a probe carrier 7 having 256 (16×16) spots in total, sixteen liquid discharging devices 1 of this type are integrally arranged on a plane to form the drawing head 8 in such a manner that 256 kinds of probe solutions in total can be discharged. The probe carrier may have at least 1,000 kinds of probes in some cases. In such a case, it is only necessary to use a drawing head constructed by integrally arranging more liquid discharging devices.

Figure 9:
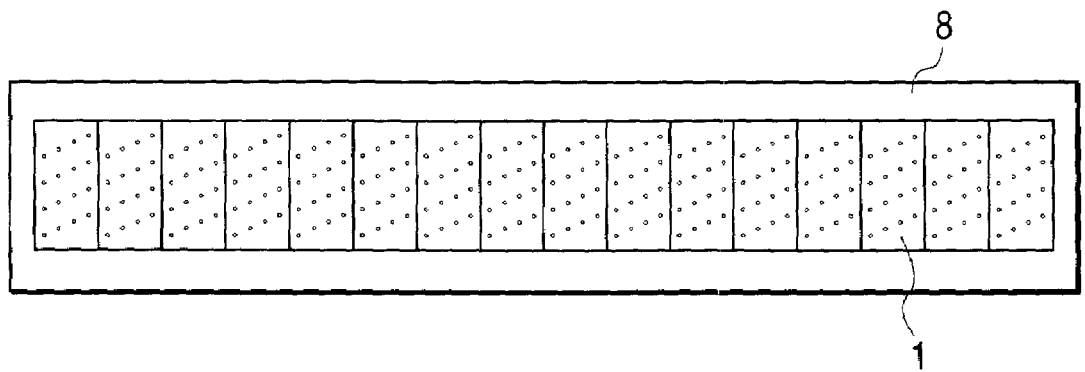
FIG. 9 illustrates an appearance of another exemplary drawing head.
Figure 10:
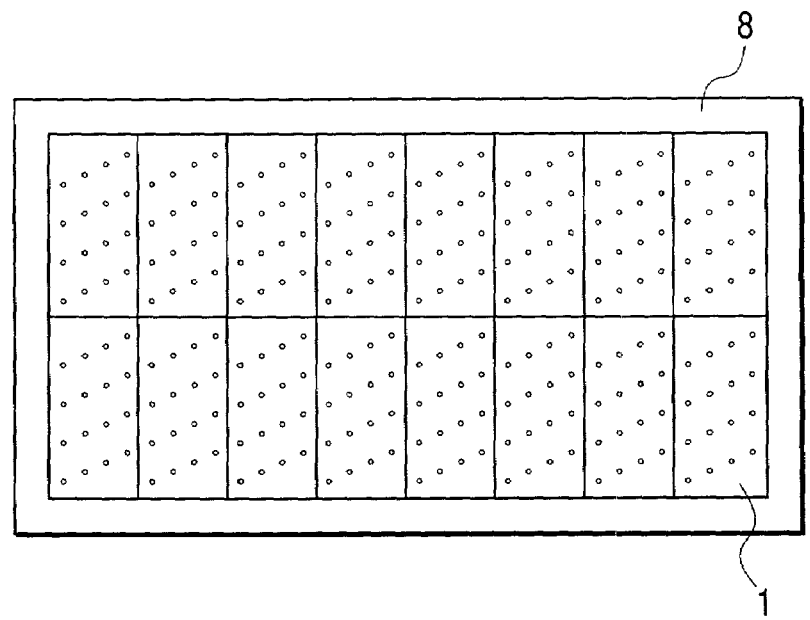
FIG. 10 illustrates an appearance of a further exemplary drawing head.

As the plane arrangement of the liquid discharging devices 1, the sixteen liquid discharging devices 1 may be arranged in a line in width as illustrated in FIG. 9. This construction has such a merit that main scanning may be performed only four times for applying the probe solutions to spots in a form of a 16×16 matrix as described below. However, the drawing head 8 becomes long from side to side. Accordingly, the drawing head 8 may be constructed by integrally arranging the liquid discharging devices 1 in 2 lines (8 in width by 2 in length) as illustrated in FIG. 10. According to this drawing head 8, however, main scanning must be performed 8 times for applying the probe solutions to spots in a form of a 16×16 matrix as described below.

Four orifices 2 standing in a row with the space of L between them as shown in FIG. 13 are communicated with one solution reservoir 4 through liquid paths 6 independent from one another as shown in FIG. 5. In other words, four nozzles 5 independent from one another are formed. A discharge heater 3 (discharge energy generating means) for causing a probe solution to be film-boiled to discharge it from the orifice 2 is arranged at a position over the orifice 2 in each nozzle 5. Accordingly, the probe solutions can be separately discharged from the respective orifices 2.

The orifices 2 are arranged at intervals P of ⅕ inches (5.08 mm) both in length and width with rows of each four orifices in length lined by four rows in width viewed on the orifices 2 having the same arrangement position in the respective liquid discharging parts among four orifices in the respective liquid discharging parts. The orifices 2 of each row are arranged with a difference by an interval of P/4 in a lengthwise direction from the orifices 2 of the adjacent row.

The probe solution is fed from the upper surface of the solution reservoir 4 by a tube or pipette to be filled into the nozzle 5. In this embodiment, the amount of a droplet discharged from the orifice 2 is about 10 p1, and the diameter of the orifice is several tens micrometers. Therefore, the probe solution fed is held in the solution reservoir 4 and nozzle 5 without leaking from the orifice 2 by virtue of a negative pressure generated in the orifice 2. The liquid path 6 is constructed extremely short. Therefore, when the probe solution is fed, the interior of the nozzle 5 is quickly filled to the orifice 2 with the probe solution. Thus, there is no need of a sucking operation for filling the probe solution into the orifice 2, and the liquid discharging device can be put into such a condition that discharge can be normally conducted much by performing preliminary discharge.

Figure 14:
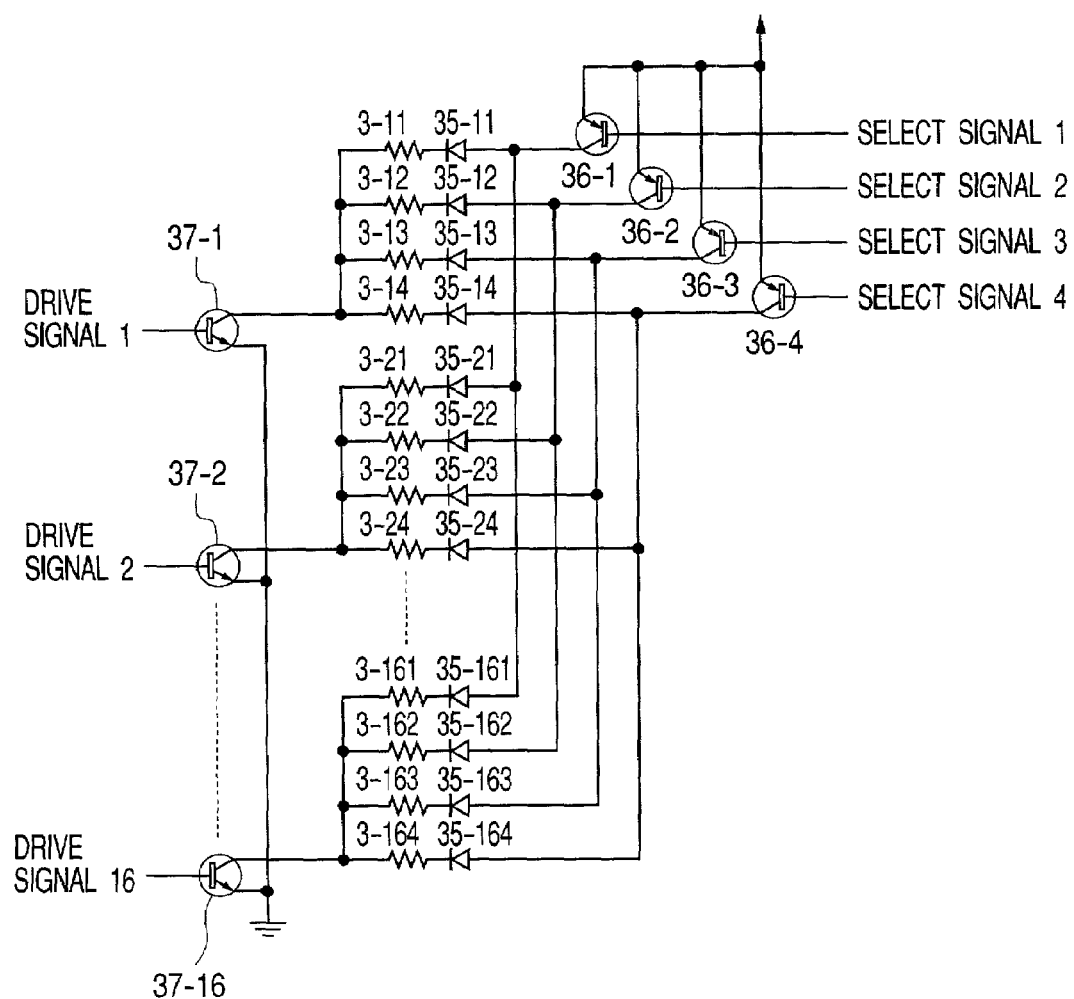
FIG. 14 illustrates a drive circuit of discharge heaters in the liquid discharging device shown in FIG. 12.

In the second embodiment of the present invention, any one of four nozzles 5 communicating with a solution reservoir 4 is selected, and a probe solution is discharged from the selected nozzle 5. FIG. 14 illustrates a drive circuit of discharge heaters 3 for performing such discharge. In FIG. 14, the respective discharge heaters 3 in four nozzles 5 communicating with the first solution reservoir 4 are shown as discharge heaters 3-11, 3-12, 3-13 and 3-14 in order from that corresponding to the lowest orifice 2 in FIG. 13. Similarly, discharge heaters 3-21 to 3-24 indicate respective discharge heaters 3 in 4 nozzles 5 communicating with the second solution reservoir 4, and discharge heaters 3-161 to 3-164 indicate those of the sixteenth solution reservoir 4. In FIG. 14, discharge heaters 3 in nozzles 5 communicating with the third to fifteenth solution reservoirs 4 are not illustrated. However, they are constructed in the same manner as the first, second and sixteenth ones.

Among the discharge heaters 3 in the nozzles 5 communicating with the respective solution reservoirs 4, one end of the discharge heaters 3-11 and 3-21 to 3-161 corresponding to the lowest orifices 2 in FIG. 13 is connected to a common wire through respective diodes 35-11 and 35-21 to 35-161. The common wire is connected to a collector electrode of a transistor 36-1. Among the discharge heaters 3 in the nozzles 5 communicating with the respective solution reservoirs 4, the discharge heaters corresponding to the second, third and fourth discharge heaters from the lowest in FIG. 13 are also connected by respective common wires in the same manner as described above, and the common wires are connected to collector electrodes of transistors 36-2, 36-3 and 36-4, respectively. In such a manner, the discharge heaters 3-1 to 3-164 are connected to those located in the same order from the lowest in FIG. 13 to form a group and divided into four groups.

Wires through which respective select signals 1 to 4 are inputted are connected to the base electrodes of transistors 36-1 to 36-4. Thus, drive voltage is applied to the common wire connected to the transistor in which a low signal has been inputted as this select signal 1, 2, 3 or 4. Only one of the select signals 1 to 4 is generally inputted as a low signal, and only one group becomes a dischargeable state On the other hand, the other ends of the discharge heaters 3 in the four nozzles 5 communicating with one solution reservoir 4 are connected to a common wire, and the common wire is connected to a collector electrode of one of transistors 37-1 to 37-16. Wires through which respective drive signals 1 to 16 are inputted are connected to the base electrodes of these transistors 37-1 to 37-16. Thus, when a drive pulse is inputted as one of the drive signals 1 to 16, the discharge heater connected to the transistor in which the drive pulse has been inputted is driven at the timing thereof. At this time, the drive voltage is applied only to the discharge heaters of the group selected by the select signal 1, 2, 3 or 4. Accordingly, only the discharge heater 3 belonging to the group selected with respect to the discharge heaters 3 in the four nozzles 5 communicating with each solution reservoir 4 is driven, and the probe solution is discharged from the nozzle in which such a discharge heater 3 is arranged.

In this embodiment, the first nozzle group is generally selected and used. When a non-discharging nozzle from which no liquid can be discharged occurs among the nozzles belonging to the first group, the second nozzle group is selected as described below, and this selection is successively switched-over to the third or fourth.

Figure 4:
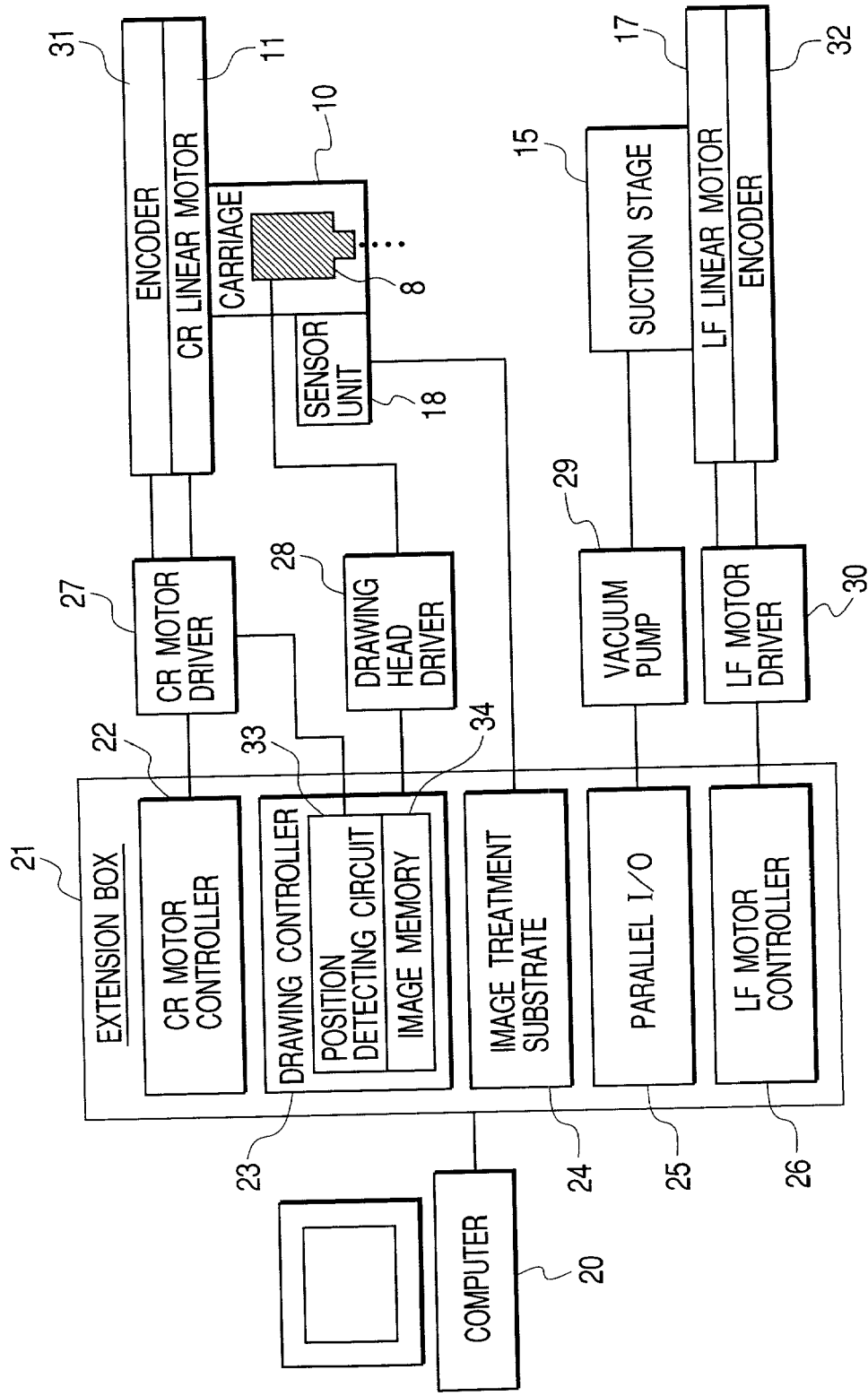
FIG. 4 is a block diagram illustrating the exemplary drawing apparatus according to the present invention.

With reference to FIG. 4, the construction of a control system of the drawing apparatus according to this embodiment will now be described. FIG. 4 is a block diagram illustrating the whole structure of the drawing apparatus. In this control system, five substrates in total are mounted in an extension box 21 of a computer 20 for every function of the drawing apparatus. The computer 20 controls these substrates to control the whole apparatus.

When movement commands of respective motors are inputted into a CR motor controller 22 and an LF motor controller 26 from the computer 20, they are separately converted into a quantity of movement and a velocity curve, which are outputted as pulse trains to a CR motor driver 27 and an LF motor driver 30. The CR motor driver 27 and LF motor driver 30 respectively control the operations of a CR linear motor 11 and an LR linear motor 17 according to the pulse trains from the controllers on the basis of the position signals of encoders 31, 32 respectively built in the linear CR motor 11 and LF linear motor 17. In this embodiment, the resolutions of the encoders 31, 32 are 0.5 μm in both CR and LF and sufficient for the spotting interval, 80 dpi (317.5 μm) of a general probe carrier.

The output of the encoder 31 in the CR linear motor 11 is also sent to a drawing controller 23 via the CR motor driver 27 and used as an input signal for a carriage position detecting circuit 33 in the drawing controller 23. The drawing controller 23 has a function for driving the driving head 8. More specifically, the drawing controller 23 has a function of storing image data sent from the computer 20 in an image memory 34 once, a function of converting the image data in the image memory 34 into discharge data for the drawing head 8 and a function of sending signals for inputting the discharge data and timing of driving the drawing head 8 to a drawing head driver 28 when the carriage position detecting circuit 33 judges that the carriage 10 has reached a drawing position.

An image treatment substrate 24 has a function of successively sampling one-dimensional image signals from the image sensor unit 18 according to movement of the carriage 10 and inputting signals obtained thereby as two-dimensional signals in an image memory in the image treatment substrate 24. In other words, the image treatment substrate 24 can input a matrix pattern image by inputting an image while the image sensor unit 18 is moving on the matrix pattern of the probe carrier 7. The computer 20 accesses the data in this image memory to perform image treatment, whereby the presence of defective spots in the matrix pattern, to which no probe solution is applied, can be detected.

A parallel I/O 25 is connected to a vacuum pump 29 which sucks the carrier 16 on the stage 15, and controls the operation of the vacuum pump according to a command from the computer 20.

Figure 8:
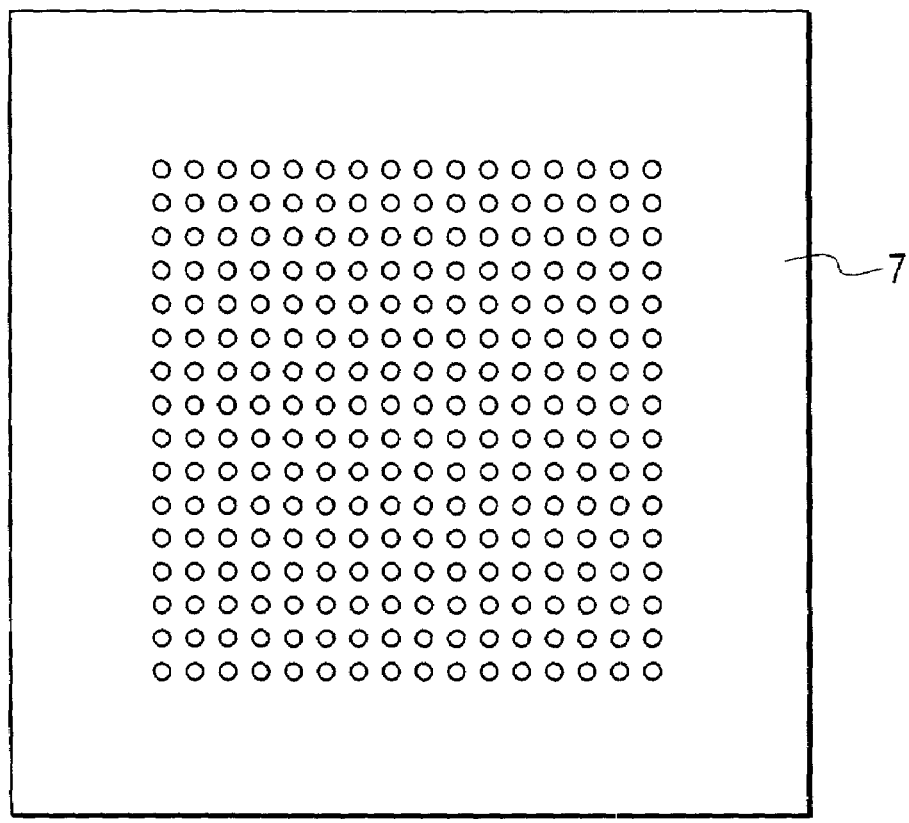
FIG. 8 illustrates an appearance of an exemplary DNA microchip.

An exemplary probe carrier 7 produced by the drawing apparatus according to this embodiment will now be described with reference to FIG. 8. FIG. 8 illustrates an appearance of the probe carrier 7. On the probe carrier 7, 256 (16×16) spots in total are arranged at intervals of 80 dpi (0.318 mm) both in length and width. Probe solutions spotted by the liquid discharging devices are applied to the respective spots. In ordinary case, all the probe solutions injected on the respective spots have compositions different from one another. A plurality of such probe carriers 7 are generally formed on the carrier 16.

In the present specification, the probes immobilized on the carrier are those capable of being specifically bonded to a specific target substance. The probes include oligonucleotides and polynucleotides which can be recognized by specific targets, and other polymers. The term "probe" as used herein means both a molecule having a probe function, such as a polynucleotide molecule and a group of molecules having the same probe function, such as a group of polynucleotides having the same sequence surface-immobilized at dispersed positions, often including molecules called ligands. The probe and target are often replaceably used. The probe may be bonded as a part of a pair of ligand and anti-ligand (may referred to as "receptor") to a target or become capable of being bonded. The probes and targets in the present invention may include bases naturally found, or analogues thereof.

As examples of the probes supported on the carrier, those having a binding site to the carrier through a linker at a part of an oligonucleotide composed of a base sequence capable of hybridizing with a target nucleic acid and a structure that is joined to the surface of the carrier at the binding site may be mentioned. Incidentally, in such a structure, the position of the oligonucleotide at the binding site to the carrier in its molecule is not particularly limited within limits not impeding a desired hybridization reaction.

Probes adopted in a probe array to which the process according to the present invention is applied are suitably selected as necessary for the end application intended. However, they are preferably at least one selected from the group consisting of DNAs, RNAs, cDNAs (complementary DNAs), PNAs, oligonucleotides, polynucleotides, other nucleic acids, oligopeptides, polypeptides, proteins, enzymes, substrates to enzymes, antibodies, epitopes to antibodies, antigens, hormones, hormone receptors, ligands, ligand receptors, oligosaccharides and polysaccharides.

In the present invention, one obtained by immobilizing plural kinds of these probes on the surface of a carrier in independent regions, for example, as dotted spots is referred to as a probe carrier, while one obtained by arranging them at predetermined intervals is referred to as "probe array".

On the other hand, it is desirable that the probes have a structure capable of being bonded to the carrier, and the immobilization of the probes on the carrier is performed through this structure capable of being bonded. At this time, the structure capable of being bonded to the surface of the carrier owned by the probes is preferably formed by a treatment that at least one of organic functional groups such as an amino group, mercapto group, carboxyl group, hydroxyl group, acid halide (haloformyl group; —COX), halide (—X), aziridine, maleimide group, succinimide group, isothiocyanate group, sulfonyl chloride group (—$SO_2Cl$), aldehyde group (formyl group; —CHO), hydrazine and acetamide iodide is introduced. The surface of the carrier may be subjected to a necessary treatment according to the structure necessary for the bonding of the probe to the carrier.

Figure 1:
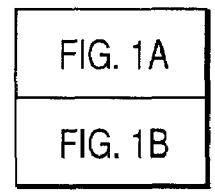
FIG. 1, which is composed of FIGS. 1A and 1B, is a flow chart illustrating an example of a drawing process according to the present invention.
Figure 1A:
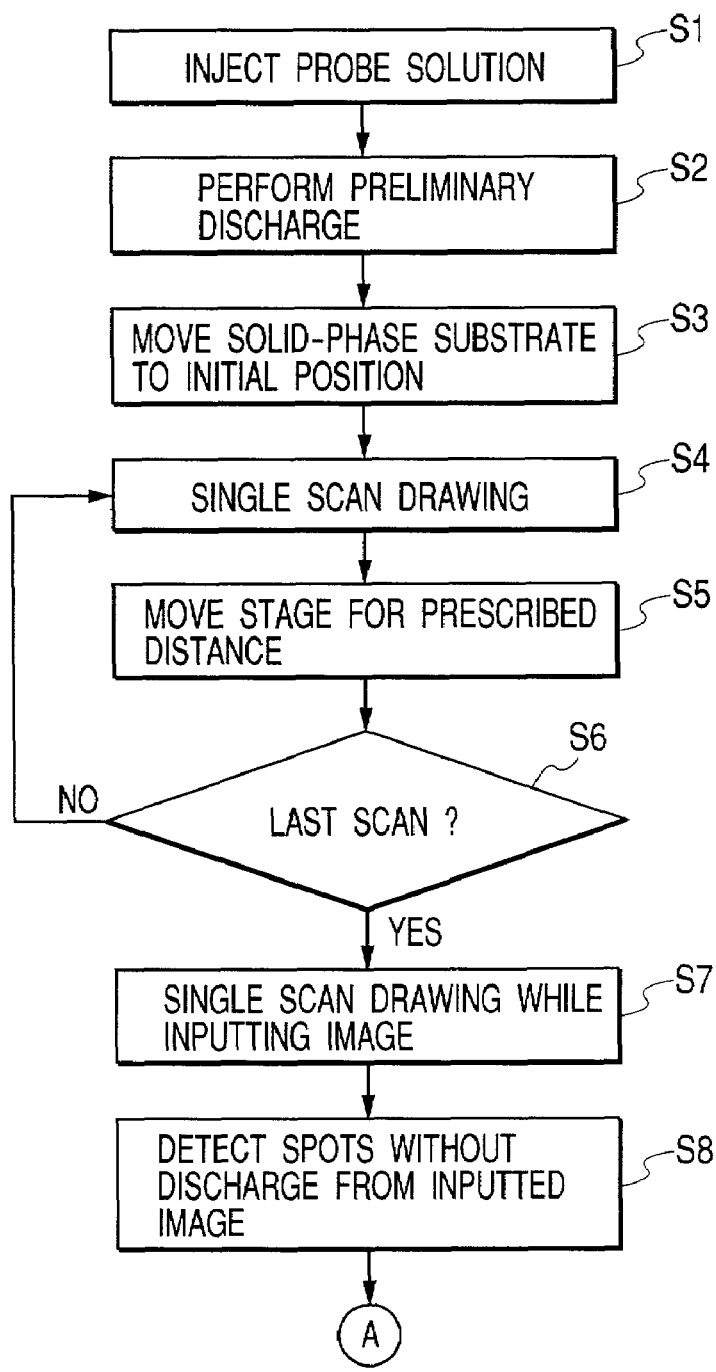

A recovery process of spots without discharge, which is a feature in the present invention, will now be described by reference to the flow chart shown in FIG. 1. When probe solutions are first injected in chip tanks 4 in step S1, preliminary discharge is performed in step S2 so as to surely fill nozzles 5 and orifices 2 with the solutions. When the preliminary discharge is completed, in step S3, a stage 15 is moved for the purpose of drawing a first matrix, a solid-phase substrate 16 is caused to stand still at a prescribed position, and moreover a carriage 10 is moved at a starting point thereof for the purpose of performing a drawing operation. In step S4, the carriage 10 starts moving in a main scanning direction for first scan drawing. When the carriage 10 passes through a drawing position to complete the drawing operation, the carriage 10 returns again to the starting position to be on standby. Since second scan drawing must be performed after a drawing head 8 is shifted by a prescribed distance from the position of the first scanning in a secondary scanning direction, the stage 15 is moved by a prescribed distance in step S5 before a drawing operation. In such a manner, scanning comes to be performed repeatedly 8 times. In the case of the last scanning (YES in step S6), an image of a matrix condition is inputted by an image sensor unit 18 while performing the drawing operation in step S7. In step S8, the image is subjected to an image treatment to detect spots without discharge (defective spots). When spots without discharge are detected (YES in step S9), a drawn image only for the spots without discharge is formed in step S11, a preliminarily discharging operation is performed only for nozzles from which the probe solutions are discharged onto the spots without discharge in step S12, and the portion of the spots without discharge is then redrawn in step S13, namely, the probe solutions are discharged and applied thereto. When plural spots without discharge are present, and the spots without discharge are dispersed and present in plural scans, a drawn image is formed every scan to perform a redrawing operation on all necessary scans. When redrawing on the spots without discharge is completed, the stage 15 moves at a final scanning position in step S14 to input an image of matrix condition again. When spots without discharge are detected from the inputted image by a treatment for detecting spots without discharge in step S15, redrawing is performed again. However, since recovery is impossible even when redrawing is performed again and again if the probe solutions are empty, or the drawing head itself is disordered, a message of abnormality is outputted to stop redrawing when the number of redrawing exceeds the prescribed number (YES in step S10). When any spots without discharge are finally eliminated by such processing sequence (NO in step S9), the solid-phase substrate is moved to the next chip position for the purpose of automatically performing a drawing operation for the next DNA microchip to conduct the same processing repeatedly. In this embodiment, preliminary discharge for spots without discharge is performed prior to the redrawing. However, the preliminary discharge can be omitted without any particular problems when discharge is comparatively stable. Even when the message of abnormality is indicated to stop the redrawing, the present chip may be recovered when the probe solutions are injected if the solutions are empty, so as to perform redrawing. Further, the detection of the spots without discharge may be performed every scan to complete the redrawing within such a scan without any problems.

Figures 2, 2A:
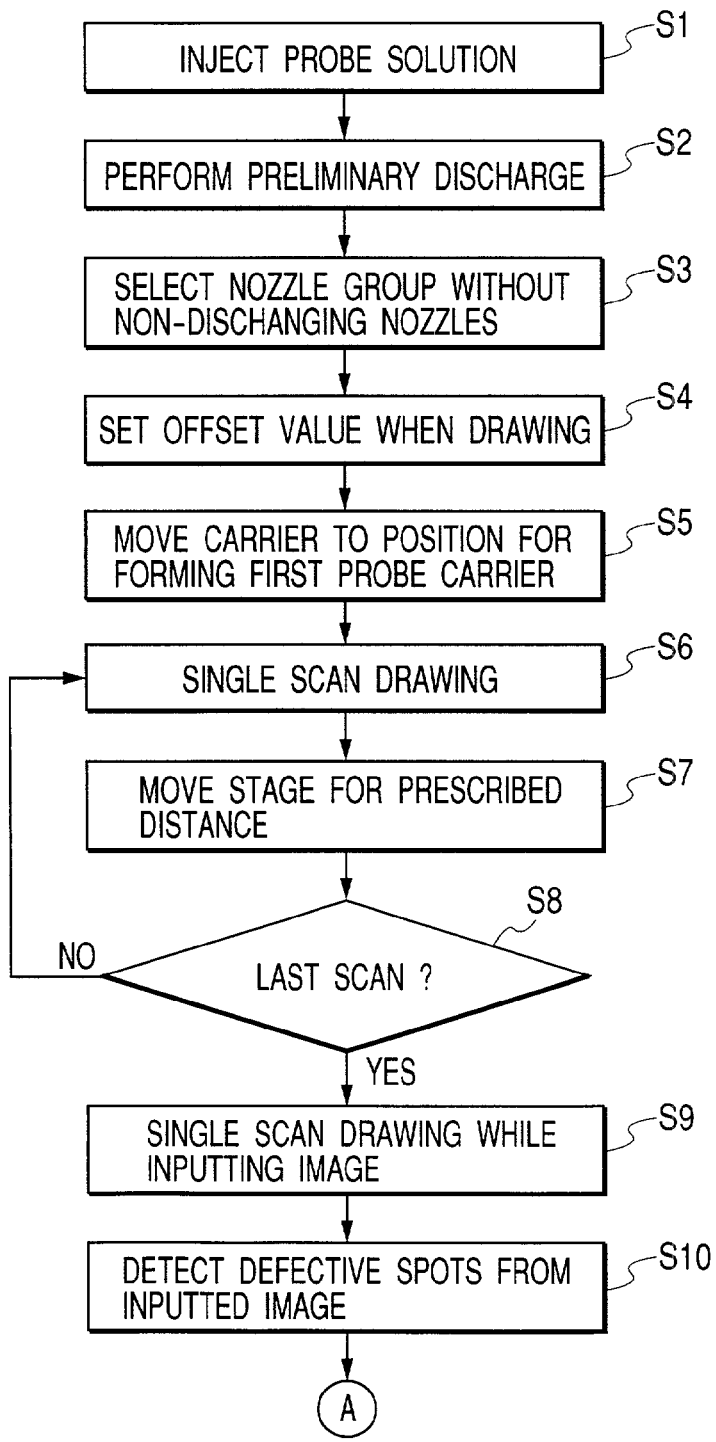
FIG. 2, which is composed of FIGS. 2A and 2B, is a flow chart illustrating a drawing process according to an embodiment of the present invention.
Figure 2B:
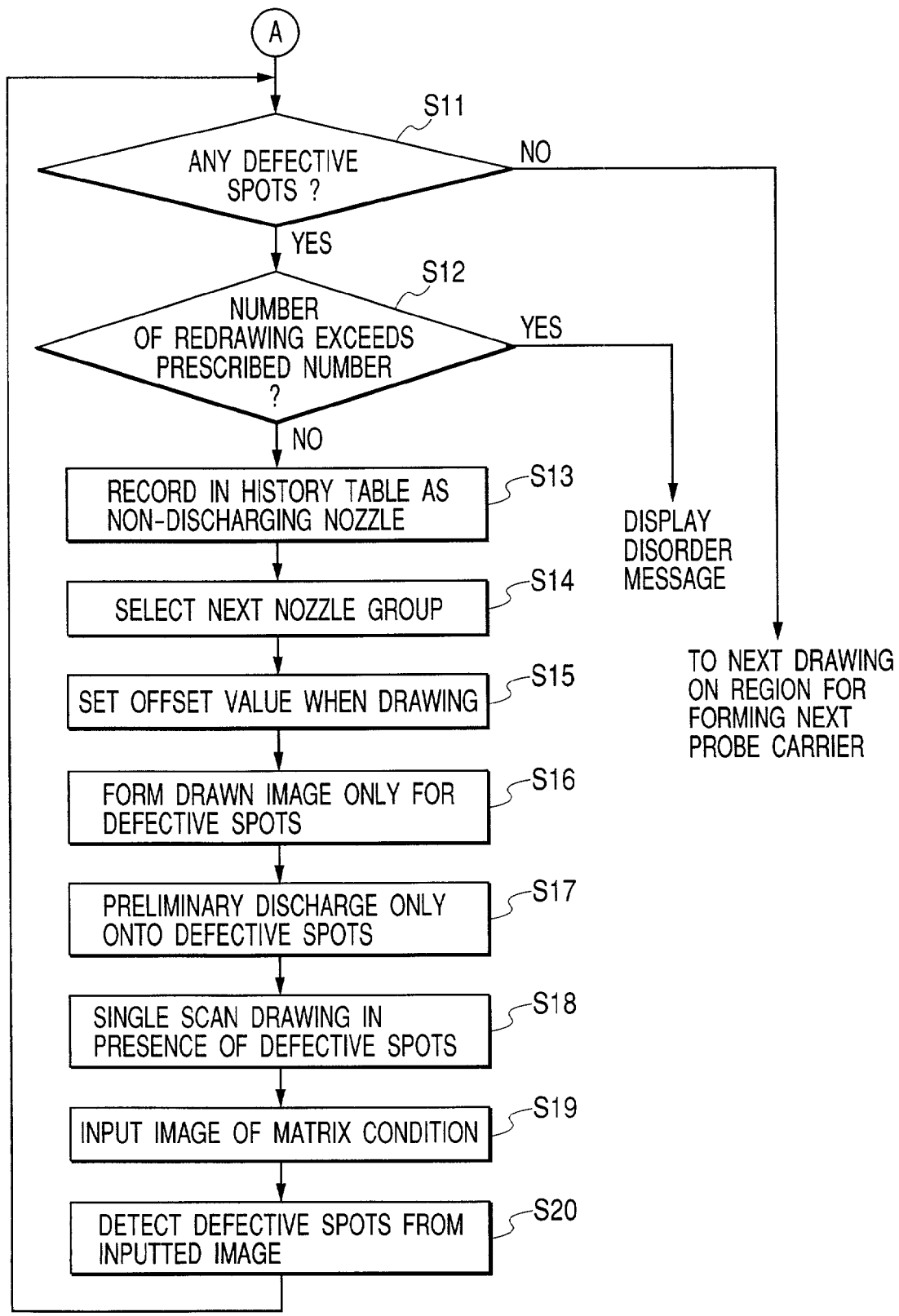

A process of producing a probe carrier 7 by using the liquid discharging device according to the second embodiment to spot probe solutions on a carrier 16 in the form of a matrix will now be described with reference to FIG. 2.

Probe solutions are first injected in solution reservoirs 4 in step S1. In step S2, preliminary discharge is performed on all nozzles 5 of four nozzle groups so as to surely fill the nozzles 5 with the probe solutions.

When the preliminary discharge is completed, in step S3, a nozzle group used is set. At this time, the first nozzle group is set when the liquid discharging devices 1 are new and without any non-discharging nozzles. When the liquid discharging devices 1 used heretofore are used, a non-discharging nozzle history table, which will be described subsequently, is researched to find a nozzle group without any non-discharging nozzles in order from the first nozzle group. When a nozzle group without any non-discharging nozzles is found, the nozzle group is set as a nozzle group to be used. The setting is performed by taking its corresponding signal among the above-described select signals 1 to 4 as a low signal.

Since the positions of orifices 2 in the nozzles 5 belonging to the respective nozzle groups are different among the nozzle groups as shown in FIG. 13 and the like, an offset value upon drawing is set in step S4 in such a manner that the probe solutions can be applied to substantially the same positions even when any nozzle group is selected. Since a first block is generally selected, the offset value when the first block is selected is regarded as, for example, 0. For example, when a second block is selected, the offset value is set to L because the positions of orifices 2 in the nozzles 5 belonging to the second nozzle group are shifted by a space L from those in the first group. Thereby, the moving position of the stage 15 in step S7 is changed to a position shifted by the offset value, L from the original moving position when the first nozzle group is selected. The probe solutions can be thereby applied to the same positions as in the case where the first nozzle group is selected even when the second nozzle group is selected.

The carrier 16 is sucked and held on the stage 15 in advance by the vacuum pump 29. In step S5, the carrier 16 is moved by the LF linear motor 17 to a starting position where a scanning passage of the carriage 10 is located at a forming position of a first probe carrier. At this time, the carriage 10 is simultaneously moved to a starting position for performing a drawing operation by the CR linear motor 11.

In step S6, the carriage 10 is then moved in a main scanning direction. At this time, single scan drawing is performed to discharge the probe solutions from the respective nozzles 5 at the prescribed timing so as to apply them to spots on the carrier 16. In step S7, the stage 15 is moved by a prescribed distance in a secondary scanning direction, and single scan drawing is then performed again. In such a manner, scanning is performed the prescribed number of times to conduct drawing, whereby the probe solutions can be applied to spots in the form of a matrix as shown in FIG. 8. In the drawing in this embodiment, plural kinds of probe solutions are always applied with a constant pattern. However, discharge data for providing this pattern may be inputted to perform drawing according to the discharge data.

At this time, the timing of discharge of the probe solutions from the respective nozzles 5 is provided by detecting the fact that the carriage 10 has reached the prescribed position by the position detecting circuit 33 of the drawing controller 23 and outputting the discharge data and drive timing signals from the drawing controller 23 to the drawing head driver 28. The drawing head driver 28 receives these signals and converts them into drive signals for actually driving the respective discharge heaters 3 to output the converted signals to the drawing head 8, whereby the drawing head 8 discharges the probe solutions on the carrier 16. What nozzle among the four nozzles 5 communicating with the respective solution reservoirs 4 is used to discharge the probe solution has been determined in step S3, and the discharge is performed from the nozzles 5 belonging to a nozzle group selected by the setting of select signals 1 to 4.

Figure 6:
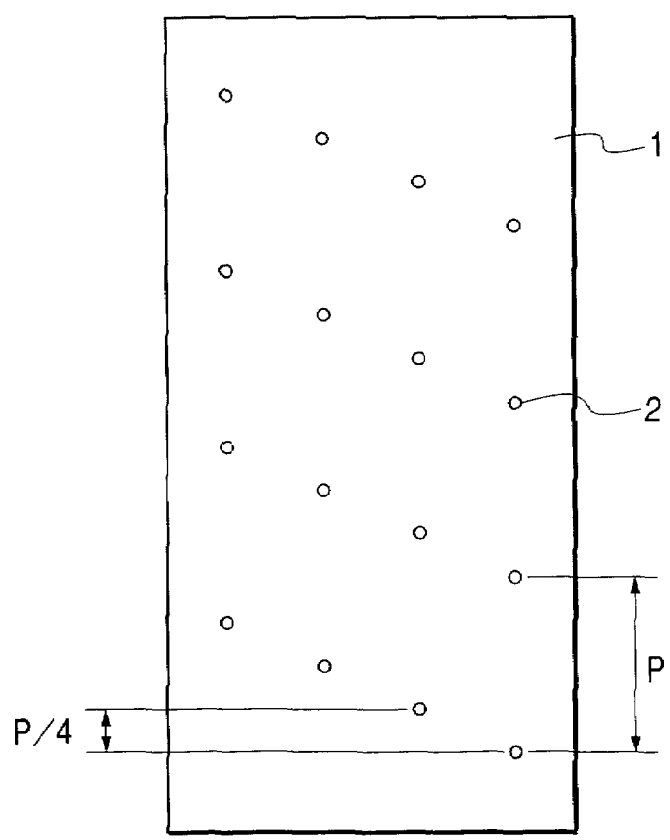
FIG. 6 illustrates an appearance of an exemplary liquid discharging device.
Figure 7:
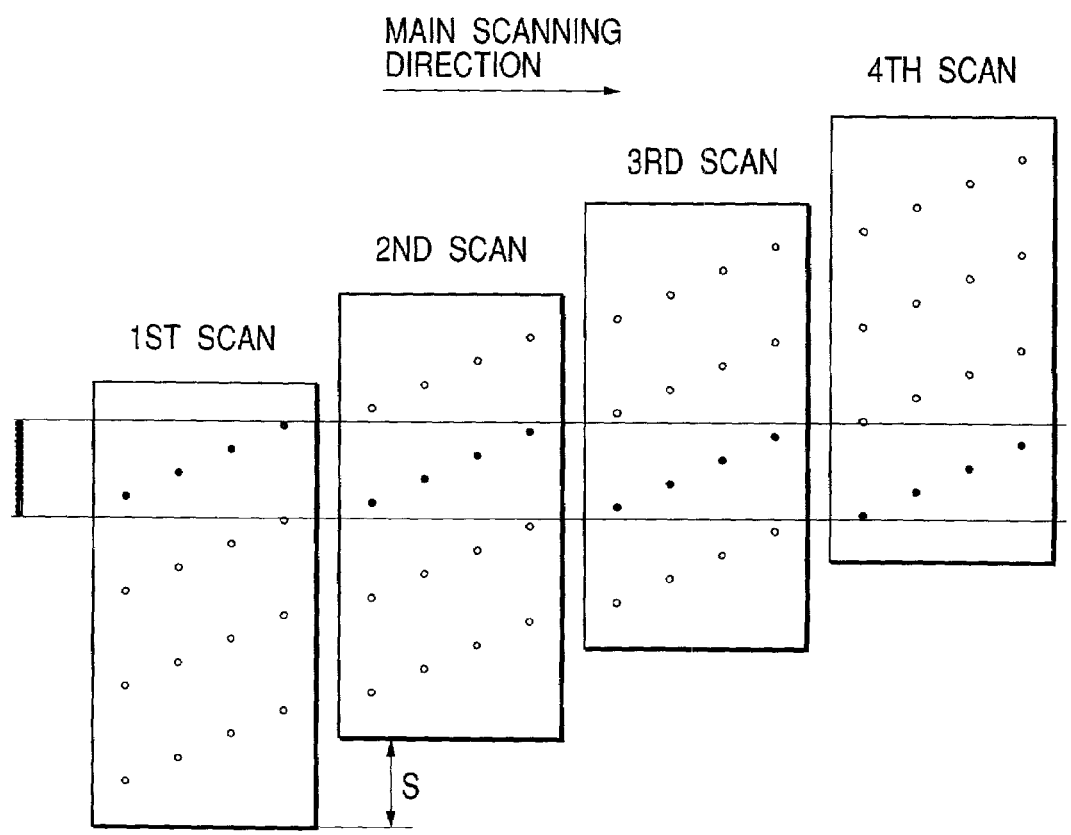
FIG. 7 illustrates an exemplary drawing process of a DNA microchip.

Here, a process of applying the probe solutions to the spots in the form of the matrix by conducting scanning plural times to perform drawing will be described. With reference to FIGS. 6 and 7, a process of applying the probe solutions to sixteen spots standing lengthwise by the liquid discharging device 4 having sixteen solution reservoirs 4 will be first described.

In the drawing apparatus according to this embodiment, one nozzle group among four nozzle groups is selected, and the probe solutions are discharged from the orifices 2 in the nozzles 5 belonging to the selected nozzle group. FIG. 6 illustrates the arrangement of the orifices 2 belonging to one nozzle group. As described above, these orifices are arranged at intervals P of ⅕ inches (5.08 mm) both in length and width with rows of each four orifices in length lined by four rows in width. The orifices 2 of each row are arranged with a difference by an interval of P/4 in a lengthwise direction from the orifices 2 of the adjacent row. Accordingly, the orifices 2 are arranged at intervals of P/4, i.e., 20 dpi (1.27 mm) viewed in the lengthwise direction. Since the spot interval of the probe carrier 7 is 80 dpi (0.318 mm) as against this nozzle pitch of 20 dpi (1.27 mm), the probe solutions cannot be applied to spots of this interval by a single scanning.

Thus, single scan drawing is performed four times to apply the probe solutions to sixteen spots standing lengthwise. FIG. 7 illustrates this process. In FIG. 7, the side of the liquid discharging device 1 is illustrated at positions shifted by a shift distance S for the purpose of intelligibly indicating changes in the relative position between the carrier 16 and the liquid discharging device 1. In the drawing apparatus of this embodiment, however, the side of the carrier 16 is actually moved.

In the first scan drawing, the probe solutions are successively discharged from upper four orifices 2 indicated by black dots in FIG. 7 at the prescribed timing while moving the liquid discharging device 1 in a main scanning direction shown by an arrow in FIG. 7, thereby applying the probe solutions to four spots standing lengthwise. At this time, the probe solutions are applied to four spots standing at intervals of 20 dpi (1.27 mm).

The stage 15 is then moved by the shifting distance S. The shifting distance at this time is determined to be 15 times the interval of 80 dpi (0.318 mm), i.e., 4.76 mm. As a result, the fifth to eighth orifices from the top in FIG. 7 come to be arranged at respective positions shifted by 0.318 mm downward from the positions of the upper four orifices 2 upon the first scan drawing viewed in the lengthwise direction. The liquid discharging device 1 is moved to the starting position upon the movement of the stage 15 in such a manner that the liquid discharging device 1 is moved from the starting position even in the second scan drawing.

In the second scan drawing, probe solutions are discharged from the fifth to eighth orifices from the top in FIG. 7 at the prescribed timing to apply the probe solutions to four spots standing lengthwise. At this time, the probe solutions are applied to four spots only 0.318 mm apart downward in FIG. 7 from the spots to which the probe solution have been applied in the first scan drawing.

Similarly, after the stage 15 is moved by the respective prescribed shifting distances S, probe solutions are discharged from the ninth to twelfth orifices 2 from the top in FIG. 7 to perform the third scan drawing, and probe solutions are discharged from the lower four orifices 2 to perform the fourth scan drawing. The probe solutions can be thereby applied to the sixteen spots standing lengthwise at intervals of 0.318 mm, i.e., 80 dpi.

When a drawing head 8 in which the sixteen liquid discharging devices 1 are integrally arranged in a line in width as illustrated in FIG. 9 is used, probe solutions are applied to sixteen spots standing lengthwise at intervals of 80 dpi (0.318 mm intervals) by four scan drawing operations by means of each liquid discharging device 1 at positions shifted by 0.318 mm in the widthwise direction between the respective liquid discharging devices 1. The probe solutions can be thereby applied to the spots in a form of a 16×16 matrix standing at intervals of 80 dpi (0.318 mm intervals) both in length and width.

When a drawing head 8 in which the liquid discharging devices 1 are integrally arranged in two lines (8 in width by 2 in length) as illustrated in FIG. 10 is used, probe solutions are applied to spots standing in 8 in width×16 in length at intervals of 80 dpi (0.318 mm intervals) both in length and width by first four scan drawing operations by means of the upper eight liquid discharging devices 1. Probe solutions are applied to the remaining spots standing in 8 in width×16 in length by subsequent 4 scan drawing operations by means of the lower 8 liquid discharging devices 1. The probe solutions can be thereby applied to the spots in a form of a 16×16 matrix standing at intervals of 80 dpi (0.318 mm intervals) both in length and width.

When the fact that the next scanning is a last scanning is detected in step S8 when scanning is performed the prescribed number of times to apply the probe solutions to the spots in the form of the 16×16 matrix, the condition images (drawn patterns) of the respective spots are inputted by the image sensor unit 18 while performing a drawing operation in step S9. In step S 10, the inputted image is subjected to an image treatment by the computer 20 to detect defective spots to which no probe solution has been applied.

When the absence of the defective spots is judged in step S11, the carrier 16 is moved in such a manner that a scanning passage of the carriage 10 is located at a forming position of a next probe carrier 7. The probe solutions are then applied to spots in the form of the matrix making up the next probe carrier 7.

When the presence of the defective spots is detected in step S11 on the other hand, the following recovery treatment is performed. In step S13, the nozzle group used in the drawing is first recorded in a non-discharging nozzle history table as non-discharging nozzles. In step S14, select signal 1, 2, 3 or 4 is switched over to select the next nozzle group. In step S15, the offset value of the drawing position is set to a value according to the selected nozzle group. The non-discharging nozzle history table is used in selection of a nozzle group first used upon production of the next probe carrier 7 as described above.

In step S16, repair image data for performing drawing only for defective spots is prepared. In step S17, preliminary discharge is performed on nozzles 5 used in discharging and applying the probe solutions to the defective spots. In step S18, redrawing is performed according to the repair image data prepared.

Since the probe solution are discharged and applied only to the defective spots in this redrawing, the redrawing is conducted by only one scanning when, for example, only one defective spot is present. More specifically, the stage 15 is moved at a position corresponding to the position upon the scanning that the probe solution is discharged and applied to the defective spot among the prescribed number of scanning operations performed upon the application of the probe solutions in the form of the 16×16 matrix, and single scan drawing is performed, whereby the probe solution can be discharged and applied to the defective spot. Even when plural defective spots are present, redrawing is performed by one scanning when all the defective spots are present at positions to which the probe solutions can be discharged and applied by one scanning. When the defective spots are dispersed and present at positions to which the probe solutions are discharged and applied by plural scanning operations on the other hand, redrawing is performed on all necessary scans.

In step S19, the condition images of the respective spots are inputted by the image sensor unit 18 while performing a drawing operation in a final scanning even when the redrawing on the defective spots is performed. In step S20, the inputted image is subjected to an image treatment by the computer 20 to detect defective spots again. When the absence of the defective spots is detected in step S11, the recovery treatment is completed to follow the application treatment of the probe solutions to spots making up the next probe carrier 7.

When the presence of the defective spots is detected in step S11 on the other hand, the selection of the next nozzle group is switched over again to perform redrawing. In such a manner, the redrawing is conducted until the defective spots are eliminated.

When the fact that defective spots are present is detected even when the number of redrawing exceeds the prescribed number, judgment that spots to which no probe solution can be applied even when any nozzle group is selected are present is given to indicate a message of abnormality to stop redrawing. This occurs in the case where the probe solutions in the solution reservoirs 4 are empty, or where all the four nozzles communicating with the solution reservoir 4 become non-discharging nozzles.

In this embodiment, preliminary discharge on the nozzles from which the probe solutions are applied to the defective spots is performed in step S16 prior to the redrawing. However, the preliminary discharge may be omitted when discharge is comparatively stable.

Even when the message of abnormality is indicated to stop the redrawing, the redrawing may be performed after the discharge and application of the probe solutions are made feasible by conducting such treatment that the probe solutions are injected if the solutions are empty. In such a manner, the recovery treatment is conducted on the probe carrier 7 not completed, whereby the probe carrier 7 can be completed, and so the production yield of the probe carrier 7 can be improved. A means for detecting the fact that the probe solutions in the solution reservoirs 4 have been reduced less than the prescribed amount may also be provided to indicate a message of a demand for injecting the probe solutions.

Further, although the detection of the defective spots is performed upon final scanning, it may be performed every scan to conduct the recovery treatment within such a scan.

As described above, four nozzles 5 communicating with one solution reservoir 4 are provided in this embodiment, one nozzle 5 among these nozzles is generally used to perform drawing, whether defective spots are present or not is detected from the spot image drawn, and the recovery treatment is conducted by means of another nozzle 5 when the presence of a defective spot is detected. The yield of the probe carrier 7 can be thereby improved to the utmost.

Since the recovery treatment is performed in such a manner, whereby the probe carrier 7 can be completed even when non-discharging nozzles occur, sucking recovery treatment for reducing the occurrence of non-discharging nozzles can be removed, and the frequency of the preliminary discharge can be lessened. The amount of the probe solutions consumed by the sucking recovery treatment and preliminary discharge can be reduced to the minimum. In addition, since no particular drawing is performed for the purpose of specifying non-discharging nozzles, the probe solutions are not wasted.

Since the drawing apparatus according to this embodiment permits reducing the consumption of liquids discharged to the minimum, it can be suitably used as a production apparatus of probe carriers using expensive probe solutions as a liquid to be discharged. However, it may also be used as another apparatus which forms images utilizing the liquid discharge devices, for example, a recording apparatus such as a printer. This embodiment is applied to such a recording apparatus, thereby bringing about effects that the quality of images formed can be improved, and the consumption of liquids for recording can be reduced to the minimum. This embodiment may also be applied to recording apparatus in which recording is conducted by other systems than liquid discharge, such as a heat-sensitive thermal head, thereby likewise bringing about the effect that the quality of images formed can be improved.

As the respective constructional elements of the liquid discharging devices and the production apparatus of the probe carriers using such devices, ink-jet recording systems for printing, and those used in heads and recording apparatus using such a system may be suitably selected for use according to the object of the present invention, or those obtained by suitably modifying them according to the object of the present invention may also be suitably used. As examples of such an ink-jet system, recording heads and recording apparatus equipped with a means (for example, electrothermal converter or laser beam) for generating thermal energy as energy used for discharging an ink, which are particularly of a system that the change of state of an ink is caused by this thermal energy, among ink-jet recording systems, may be mentioned. Excellent effects can be brought about by utilizing the constitution used in these. According to such a system, high-density recording and high definition of recording can be achieved.

Such typical constitution and principle are disclosed in, for example, U.S. Pat. Nos. 4,723,129 and 4,740,796 as a basic principle. This system may be applied to both so-called on-demand type and continuous type systems. However, it is particularly effectively applied to the on-demand type because at least one drive signal for undergoing rapid temperature rise exceeding nucleate boiling is applied to an electrothermal converter arranged in opposition to a sheet or liquid path, in which a liquid (ink) is held, in response to recording information, thereby generating thermal energy by the electrothermal converter to generate film boiling on the heat acting surface of a recording head, and consequently a bubble can be formed in the liquid (ink) corresponding one to one to this drive signal. The liquid (ink) is discharged through a discharging opening by the growth and contraction of this bubble to form at least one droplet. Since the growth and contraction of this bubble are immediately and suitably conducted when this drive signal is made a pulse form, the discharge of the liquid (ink) excellent in responsiveness in particular can be achieved. It is hence more preferable to use such a pulse signal. As such drive signal of the pulse form, that described in U.S. Pat. Nos. 4,463,359 and 4,345,262 is suitable. When the conditions described in U.S. Pat. No. 4,313,124, which discloses an invention relating to the rate of temperature rise on the above-described heat acting surface, are adopted, excellent recording can be performed.

The constructions of a recording head include combined constructions (linear liquid path or right-angle liquid path) of a discharge opening, a liquid path and an electrothermal converter. Besides, the constructions described in U.S. Pat. Nos. 4,558,333 and 4,459,600, which disclose the construction in which a heat acting part is arranged in a curved region, are also included in the present invention. In addition, the constructions based on Japanese Patent Application Laid-Open No. 59-123670, which discloses the construction in which a slit common to plural electrothermal converters is provided as a discharge part for the electrothermal converters, and Japanese Patent Application Laid-Open No. 59-138461, which discloses the construction in which an opening absorbing the pressure wave of thermal energy is opposed to a discharge part, are also effective for the effects of the present invention. In other words, according to the present invention, recording can be efficiently performed with certainty even when a recording head of any form is used.

Further, the present invention can be effectively applied to a full-line type recording head having a length corresponding to the maximum width of a recording medium on which recording can be made by a recording apparatus. Such a recording head may be either the construction in which the length is satisfied by the combination of plural recording heads or the construction as one recording head integrally formed.

The present invention is effective when among serial type recording heads, a recording head fixed to an apparatus body, a replaceable chip type recording head that is installed in an apparatus body, whereby electrical connection to the apparatus body and feeding of an ink from the apparatus body become feasible, or a cartridge type recording head in which an ink tank is integrally provided in the recording head itself is used.

The addition of a discharge-recovery means for the recording head, preliminary auxiliary means, etc., as components of the recording apparatus is preferred because the effects of the present invention can be more stabilized. Specific examples thereof include capping means for the recording head, cleaning means, pressuring or sucking means, preliminarily heating means using an electrothermal converter, another heating element or a combination thereof, and preliminarily discharging means for discharge separate from recording.

What is claimed is:

1. A production apparatus for producing a probe carrier by discharging plural kinds of liquids respectively containing plural kinds of probes capable of being specifically bonded to a target substance on a carrier, comprising:
    a liquid discharging device having nozzles for discharging the liquids respectively containing the plural kinds of probes capable of being specifically bonded to the target substance on the carrier;
    positioning means for determining a relative position between said liquid discharging device and the carrier, said positioning means comprising a stage for placing the carrier thereon and a first driver for moving the carrier in a secondary scanning direction parallel to a liquid-application surface thereof and substantially perpendicular to a main scanning direction;
    an application information detector to detect application information of the liquids discharged on the carrier on the stage from said liquid discharging device on the basis of discharge data;
    a defective spot detector for detecting defective spots where the liquids are not applied but where the respective liquids should have been applied by comparing the discharge data with the application information detected by said application information detector;
    discharge data forming means for forming discharge data as to the defective spots on the basis of defective spot information from said defective spot detector; and
    a processor for counting a number of redrawings,
    wherein said liquid discharging device executes redrawing according to the discharge data formed by said discharge data forming means by respectively applying the liquids to the defective spots on the carrier on the stage from a nozzle which is different from a nozzle that caused the defective spots, and
    wherein when the number of redrawings exceeds a prescribed number a message of abnormality is outputted to stop redrawing.

2. The production apparatus according to claim 1, wherein at least two of the nozzles are provided in said liquid discharge device for each of the plural kinds of liquids, a liquid discharge driver for driving said liquid discharging device to apply the liquid to a defective spot detected by said defective spot detector is further provided, and said liquid discharge driver drives said liquid discharging device to apply to the defective spot the same kind of a liquid as the liquid to be applied to the defective spot from a nozzle different from a nozzle from which a discharging operation of the liquid was to have been performed on the basis of the discharge data, among the at least two nozzles provided for each of the plural kinds of liquids.

3. The production apparatus according to claim 1, wherein said positioning means comprises a second driver for moving said liquid discharging device in a main scanning direction parallel to a liquid-application surface of the carrier, and further comprising a position detector to detect the position of said liquid discharging device in the main scanning direction,
    a controller for controlling discharging of the liquid on the carrier from one of the nozzles of said liquid discharging device on the basis of the discharge data, said controller determines when the liquid can be applied to the carrier according to the discharge data from position information detected by said position detector while moving said liquid discharging device in the main scanning direction, so as to drive said liquid discharging device, and
    said second driver, which drives said liquid discharging device to the defective spot to apply the liquid thereto, determines when the liquid can be applied to the defective spot from the position information detected by the position detector while moving said liquid discharging device in the main scanning direction, so as to drive the liquid discharging device.

4. The production apparatus according to claim 1, further comprising a preliminarily discharge controller for performing preliminary discharge of the liquids from said liquid discharging device.

5. The production apparatus according to claim 1, wherein said application information detector comprises a line sensor.

6. The production apparatus according to claim 1, wherein said liquid discharging device comprises a thermal energy generator which applies thermal energy to discharge the liquids.

7. A process for producing a probe carrier by discharging plural kinds of liquids respectively containing plural kinds of probes capable of being specifically bonded to a target substance on a carrier, comprising the steps of:
    (i) respectively discharging the plural kinds of liquids from a liquid discharging device on the basis of discharge data while changing a relative position between the liquid discharging device and the carrier, thereby applying the liquids to the carrier;
    (ii) detecting application information of the liquids applied to the carrier by a detection device;
    (iii) detecting defective spots where the liquids are not applied, to which defective spots the respective liquids should have been applied on the basis of the discharge data, by comparing the discharge data with the detected application information;
(iv) redrawing by discharging the liquids to the detected defective spots from a nozzle, which is different from a nozzle that caused the defective spots, of the liquid discharging device when the defective spots are detected, thereby applying the liquids to the defective spots; and
(v) counting a number of redrawings
wherein at least said steps (i), (ii), and (iv) are conducted with the carrier placed on a stage attached to an apparatus comprising the liquid discharging device and the detection device,
wherein said step (i) of discharging the liquids to the carrier on the basis of the discharge data and said step (iv) of discharging the liquids to the defective spots further comprise the step of moving the carrier in a secondary scanning direction parallel to a liquid-application surface thereof and perpendicular to a main scanning direction, and
wherein when the number of redrawings exceeds a prescribed number a message of abnormality is outputted to stop redrawing.

8. The production process according to claim 7, wherein the liquid discharging device comprises plural nozzles for each of the plural kinds of the liquids, and the same kind of a liquid as the liquid to be applied to a defective spot is applied to the defective spot from a nozzle different from a nozzle from which the discharging operation of the liquid was to have been performed on the basis of the discharge data, among the plural nozzles provided for each kind of the liquids.

9. The production process according to claim 7, wherein the liquid discharging device comprises plural nozzles and the process further comprises the step of performing preliminary discharge on those of the plural nozzles that caused the defective spots prior to said step (iv) of discharging the liquids to the defective spots.

10. The production process according to claim 7, wherein the liquid discharging device comprises plural nozzles and the process further comprises the step of performing preliminary discharge on all the nozzles of the liquid discharge device used prior to said step (ii) of detecting the application information of the liquids applied to the carrier according to the discharge data.

11. The production process according to claim 7, wherein the liquid discharging device comprises a thermal energy generator which applies thermal energy for discharging the liquid.

12. The production process according to claim 7, wherein said step (i) of discharging the liquids to the carrier on the basis of the discharge data and said step (ii) of discharging the liquids to the defective spots comprise the steps of moving the liquid discharging device in a main scanning direction parallel to a liquid-application surface of the carrier, and detecting the position of the liquid discharging device in the main scanning direction,
in the step (i) of discharging the liquids to the carrier on the basis of the discharge data, timings that the liquids can be discharged to the cater according to the discharge data are judged from position information detected by the position detector while moving the liquid discharging device in the main scanning direction, so as to discharge the liquids, and
in the step (iv) of discharging the liquids to the defective spots, timings that the liquid can be discharged to the defective spots are judged from the position information detected by the position detector while moving the liquid discharging device in the main scanning direction, so as to discharge the liquids.

13. The production process according to claim 7, wherein the liquid discharging device comprises plural nozzles and the process further comprises the step of performing preliminary discharge in which the liquids are discharged from the liquid discharging device without discharging the liquids to the carrier on all of the nozzles of the liquid discharging device prior to said step (i) of discharging the liquids to the carrier on the basis of the discharge data.

14. The production process according to claim 7, wherein the detection step (iii) is conducted based on when the liquids are finally applied in the step (ii).

15. A production apparatus for producing a probe carrier by discharging plural kinds of liquids respectively containing plural kinds of probes capable of being specifically bonded to a target substance on a carrier, comprising:
a liquid discharging device having nozzles in different nozzle groups for discharging the liquids respectively containing the plural kinds of probes capable of being specifically bonded to the target substance on the carrier;
a positioning means for determining a relative position between said liquid discharging device and the carrier, said positioning means comprises a driver for moving the carrier in a secondary scanning direction parallel to a liquid-application surface thereof and substantially perpendicular to a main scanning direction;
an application information detector that detects application information of a liquid to be discharged on the carrier from said liquid discharging device on the basis of discharge data;
a defective spot detector for detecting defective spots, the defective spots being positions where the liquids are not applied, but where the liquids should be applied according to comparison of the discharge data with the application information detected by said application information detector;
discharge data forming means for forming discharge data as to the defective spots on the basis of defective spot information from said defective spot detector; and
a processor for counting a number of redrawings,
wherein said discharge data forming means comprises means for switching-over to a nozzle from a next nozzle group, to execute redrawing from the nozzle by applying the liquids respectively to the defective spots according to the discharge data formed by said discharge data forming means, when a non-discharging nozzle from which no liquid can be discharged has occurred among the nozzles of a previous nozzle group, and
wherein when the number of redrawings exceeds a prescribed number a message of abnormality is outputted to stop redrawing.

16. The production apparatus according to claim 3, wherein said application information detector inputs a two-dimensional image according to the scanning of said liquid discharging device.

17. A process for producing a probe carrier by discharging plural kinds of liquids respectively containing plural kinds of probes capable of being specifically bonded to a target substance on a carrier, comprising the steps of:
respectively discharging the plural kinds of liquids from nozzles in different nozzle groups of a liquid discharging device on the basis of discharge data while changing a relative position between the liquid discharging device and the carrier, thereby applying the liquids to the carrier;

detecting application information of the liquids applied to the carrier;

detecting defective spots where the liquids are not applied, to which spots the respective liquids should be applied on the basis of the discharge data, by comparing the discharge data with the detected application information; and redrawing by discharging the liquids to the detected defective spots from a nozzle from a next nozzle group, thereby applying the liquids to the defective spots, when a non-discharging nozzle from which no liquid can be discharged has occurred among the nozzles of a previous nozzle group, wherein when the number of redrawings exceeds a prescribed number a message of abnormality is outputted to stop redrawing, and wherein discharging the liquids to the carrier on the basis of the discharge data and discharging the liquids to the defective spots further comprise the step of moving the carrier in a secondary scanning direction parallel to a liquid-application surface thereof and perpendicular to a main scanning direction.

18. The production apparatus according to claim 1, wherein the nozzles constitute a nozzle group comprised of a plurality of nozzles communicating with a same reservoir.

19. The production apparatus according to claim 18, wherein the plurality of nozzles of the nozzle group are arranged in a direction perpendicular to a main scanning direction of said liquid discharging device.

20. The production apparatus according to claim 3, wherein an image is inputted based on the scanning of said liquid discharging device in the main scanning direction.

21. The production apparatus according to claim 3, wherein an image is inputted based on a final scanning in the main scanning direction in a discharging operation by said liquid discharging device.

* * * * *